United States Patent [19]

Hofer et al.

[11] 4,125,609
[45] Nov. 14, 1978

[54] O-ALKYL-O-[1,6-DIHYDRO-1-SUBSTITUTED-6-THIOXOPYRIDAZIN(3)YL]-(THIONO)(THIOL) PHOSPHORIC (PHOSPHONIC) ACID ESTER AND ESTERAMIDES

[75] Inventors: Wolfgang Hofer; Fritz Maurer; Hans-Jochem Riebel, all of Wuppertal; Ingeborg Hammann, Cologne; Wolfgang Behrenz, Overath; Bernhard Homeyer, Leverkusen, all of Germany

[73] Assignee: Bayer Aktiengesellschaft, Leverkusen, Germany

[21] Appl. No.: 763,741

[22] Filed: Jan. 28, 1977

[30] Foreign Application Priority Data

Feb. 3, 1976 [DE] Fed. Rep. of Germany ....... 2603993

[51] Int. Cl.² .......................... C07D 9/65; A01N 9/36
[52] U.S. Cl. ..................................... 424/200; 544/232; 544/240
[58] Field of Search ................. 424/200; 260/250 AP; 544/232

[56] References Cited

U.S. PATENT DOCUMENTS

| 2,759,937 | 8/1956 | DuBreuil | 260/250 AP |
| 3,100,206 | 8/1963 | Ringterink | 260/250 AP |
| 3,310,560 | 3/1967 | Schönbeck | 260/250 AP |
| 3,773,766 | 11/1973 | Schmidt | 260/250 AP |
| 4,013,657 | 3/1977 | Hofer et al. | 260/250 AP |

FOREIGN PATENT DOCUMENTS

| 47/20,025 | 7/1972 | Japan | 260/250 |
| 1,232,564 | 5/1971 | United Kingdom | 260/250 |

*Primary Examiner*—Jose Tovar
*Assistant Examiner*—Mark L. Berch
*Attorney, Agent, or Firm*—Sprung, Felfe, Horn, Lynch & Kramer

[57] ABSTRACT

O-Alkyl-O-[1,6-dihydro-1-substituted-6-thioxopyridazin(3)yl]-(thiono) (thiol) phosphoric (phosphonic) acid esters and ester-amides of the formula

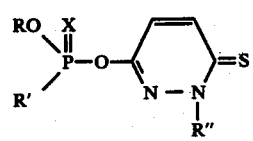

(I), in which
R is alkyl with 1 to 6 carbon atoms,
R' is alkyl, alkoxy, alkylmercapto or alkylamino with 1 to 6 carbon atoms per alkyl chain, or phenyl,
R" is alkyl, cyanoalkyl, carbalkoxyalkyl or alkylcarbonylalkyl with 1 to 4 carbon atoms per alkyl chain, phenyl or phenyl carrying at least one substituent selected from the group consisting of halogen, nitro, alkyl with 1 to 4 carbon atoms and halogenoalkyl with 1 to 4 carbon atoms, and
X is oxygen or sulfur, which possess arthropodicidal properties.

10 Claims, No Drawings

O-ALKYL-O-[1,6-DIHYDRO-1-SUBSTITUTED-6-THIOXOPYRIDAZIN(3)YL]-(THIONO) (THIOL) PHOSPHORIC (PHOSPHONIC) ACID ESTER AND ESTERAMIDES

The present invention relates to and has for its objects the provision of particular new O-alkyl-O-[1,6-dihydro-1-substituted-6-thioxopyridazin(3)yl]-(thiono) (thiol) phsophoric (phosphonic) acid ester and ester-amides which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 2,759,937 that (thiono)pyridazinephosphoric acid esters, for example O,O-dimethyl- and O,O-diethyl-O-(1,6-dihydro-6-oxo-1-phenyl-pyridazin(3)yl)-phosphoric and -thionophosphoric acid ester, possess insecticidal and acaricidal properties.

The present invention now provides, as new compounds, the (thiono)(thiol) pyridazinephosphoric (phosphonic) acid esters and ester-amides of the general formula

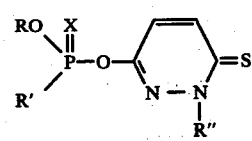

in which
R is alkyl with 1 to 6 carbon atoms,
R' is alkyl, alkoxy, alkylmercapto or alkylamino with 1 to 6 carbon atoms per alkyl chain, or phenyl,
R" is alkyl, cyanoalkyl, carbalkoxyalkyl or alkylcarbonylalkyl with 1 to 4 carbon atoms per alkyl chain, phenyl or phenyl carrying at least one substituent selected from the group consisting of halogen, nitro, alkyl with 1 to 4 carbon atoms and halogenoalkyl with 1 to 4 carbon atoms, and
X is oxygen or sulfur.

Preferably, R represents straight-chain or branched alkyl with 1 to 4 carbon atoms, R' represents straight-chain or branched alkyl, alkoxy, alkylmercapto or monoalkylamino, each with 1 to 4 carbon atoms per alkyl chain, or represents phenyl, R" represents methyl, ethyl, n-propyl, isopropyl, 2-cyanoethyl, 2-cyano-1-methyl-ethyl, cyanomethyl, or carbalkoxyalkyl or alkylcarbonylalkyl each with 1 to 3 carbon atoms per alkyl chain, or represents phenyl which can optionally be carrying one or more substituents selected from chlorine, nitro, methyl, ethyl and trifluoromethyl, and X represents sulfur.

Surprisingly, the (thiono)(thiol)pyridazinephosphoric(phosphonic) acid esters and ester-amides according to the invention exhibit a better insecticidal and acaricidal action than the previously known compounds of analogous structure and of the same type of action. The products of the present invention thus represent a genuine enrichment of the art.

The present invention also provides a process for the preparation of a (thiono)(thiol)pyridazinephosphoric(phosphonic) acid ester or ester-amide of the formula (I), in which (a) a (thiono)(thiol)phosphoric(phosphonic) acid ester halide or ester-amide halide of the general formula

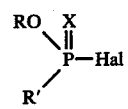

in which
R, R' and X have the above-mentioned meanings, and Hal is halogen, preferably chlorine,
is reacted with a 1,6-dihydro-3-hydroxy-6-thioxopyridazine derivative of the general formula

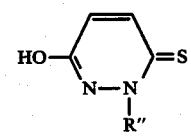

in which
R" has the above-mentioned meaning,
if appropriate in the presence of a solvent and, if appropriate, in the presence of an acid acceptor, or (b) a (thiono)(thiol)pyridazinephosphoric(phosphonic)acid ester or ester-amide of the general formula

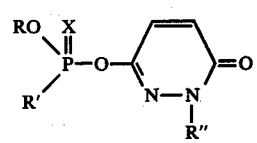

in which
R, R', R" and X have the above-mentioned meanings, is reacted with phosphorus pentasulfide in the presence of a weakly basic compound.

If, for example, O-ethyl-S-isopropyl-thionothiolphosphoric acid diester chloride and 1-phenyl-3-hydroxy-6-thioxopyridazine or O-ethyl-S-isopropyl-O-(1-phenyl-6-oxo-pyridazin(3)yl)-thionothiolphosphoric acid ester and phosphorus pentasulfide are used as starting materials, the course of the reaction can be represented by the following equations:

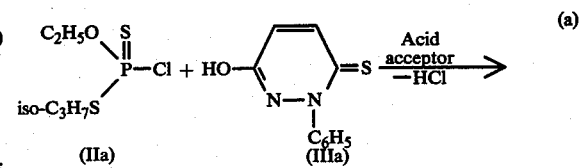

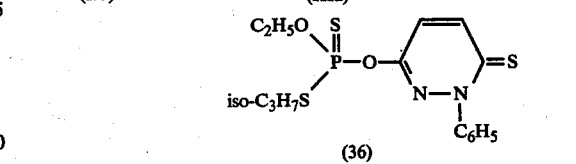

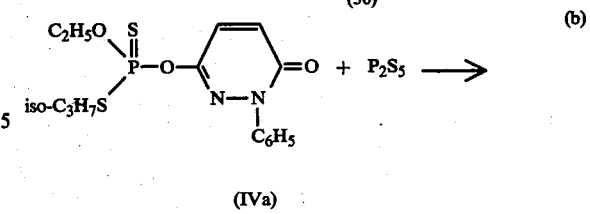

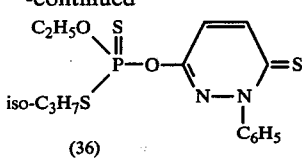

(36)

The (thiono)(thiol)phosphoric(phosphonic) acid ester halides and ester-amide halides (II) to be used as starting materials are known and can be prepared according to customary methods, even on an industrial scale.

The following may be mentioned as individual examples: O,O-dimethyl-, O,O-diethyl-, O,O-di-n-propyl-, O,O-di-iso-propyl-, O,O-di-n-butyl-, O,O-di-sec.-butyl-, O,O-di-iso-butyl-, O-methy-O-ethyl-, O-ethyl-O-n-propyl-, O-ethyl-O-iso-propyl-, O-ethyl-O-n-butyl-, O-ethyl-O-tert.-butyl-, O-ethyl-O-tert.-butyl-, O-n-propyl-O-n-butyl-, O-n-propyl-O-tert.-butyl- and O-n-propyl-O-sec.-butyl-phosphoric acid ester chloride and the corresponding thiono analogues; O-methyl-S-methyl-, O-methyl-S-ethyl-, O-methyl-S-n-propyl-, O-methyl-S-iso-propyl-, O-methyl-S-butyl-, O-ethyl-S-methyl-, O-ethyl-S-ethyl-, O-ethyl-S-n-propyl-, O-ethyl-S-iso-propyl-, O-ethyl-S-butyl-, O-n-propyl-S-methyl-, O-n-propyl-S-ethyl-, O-n-propyl-S-n-propyl-, O-n-propyl-S-iso-propyl-, O-n-propyl-S-butyl-, O-iso-propyl-S-methyl-, O-iso-propyl-S-ethyl-, O-iso-propyl-n-propyl-, O-iso-propyl-S-iso-propyl-, O-iso-propyl-S-butyl, O-n-butyl-S-methyl-, O-n-butyl-S-ethyl-, O-n-butyl-S-n-propyl-, O-n-butyl-S-iso-propyl-, O-n-butyl-O-butyl-, O-sec.-butyl-S-methyl-, O-sec.-butyl-S-ethyl-, O-sec.-butyl-S-n-propyl-, O-sec.-butyl-S-iso-propyl-, O-sec.-butyl-S-n-butyl-, O-iso-butyl-S-ethyl-, O-iso-butyl-S-n-propyl-, O-iso-butyl-S-iso-propyl-, O-tert.-butyl-S-ethyl- and O-tert.-butyl-S-n-propylthiolphosphoric acid ester chloride and the corresponding thiono analogues; O-methyl-N-methyl-, O-methyl-N-ethyl-, O-methyl-N-n-propyl-, O-methyl-N-iso-propyl-, O-methyl-N-butyl-, O-ethyl-N-methyl-, O-ethyl-N-ethyl-, O-ethyl-N-n-propyl-, O-ethyl-N-iso-propyl-, O-ethyl-N-n-butyl-, O-ethyl-N-sec.-butyl-, O-ethyl-N-iso-butyl-, O-ethyl-N-tert.-butyl-, O-n-propyl-N-methyl-, O-n-propyl-N-ethyl-, O-n-propyl-N-n-propyl-, O-n-propyl-N-iso-propyl-, O-n-propyl-N-butyl-, O-iso-propyl-N-methyl-, O-iso-propyl-N-ethyl-, O-iso-propyl-N-n-propyl-, O-iso-propyl-N-iso-propyl-, O-iso-propyl-N-butyl-, O-n-butyl-N-methyl-, O-n-butyl-N-ethyl-, O-n-butyl-N-n-propyl-, O-n-butyl-N-iso-propyl-, O-n-butyl-N-butyl-, O-sec.-butyl-N-ethyl-, O-sec.-butyl-N-n-propyl-, O-n-butyl-N-iso-propyl-, O-iso-butyl-N-methyl-, O-iso-butyl-N-ethyl-, O-iso-butyl-O-n-propyl-, O-iso-butyl-N-iso-propyl-, O-tert.-butyl-N-methyl-, O-tert.-butyl-N-ethyl-, O-tert.-butyl-N-n-propyl-, O-tert.-butyl-N-iso-propyl-, O-tert.-butyl-N-n-butyl- and O-tert.-butyl-N-iso-butylphosphoric acid ester-amide chloride and the corresponding thiono analogues; and O-methyl-, O-ethyl-, O-n-propyl-, O-iso-propyl-, O-n-butyl-, O-iso-butyl-, O-sec.-butyl- and O-tert.-butyl-methane-, -ethane-, -n-propane-, -iso-propane-, -n-butane-, -iso-butane-, -sec.-butane-, -tert.-butane- and -benzene-phosphonic acid ester chloride and the corresponding thiono analogues.

The 1,6-dihydro-3-hydroxy-6-thioxo-pyridazine derivatives (III) to be used as starting materials can be prepared from the known 1,6-dihydro-3-chloro-6-oxopyridazine derivatives (for their preparation, see K. Eichenberger et al., Helv.Chim. Acta 37, 837 (1954)) by reaction with phosphorus pentasulfide followed by saponification, in accordance with the following equation:

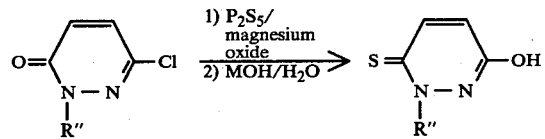

wherein
R" has the above-mentioned meaning and
M represents sodium or potassium.

The following may be mentioned as individual examples: 1-methyl-, 1-ethyl-, 1-n-propyl-, 1-iso-propyl-, 1-(2-cyanoethyl)-, 1-(1-cyanoethyl)-, 1-cyanomethyl-, 1-phenyl-, 1-(3-chlorophenyl)-, 1-(2-chlorophenyl)-, 1-(4-chlorophenyl)-, 1-(3-nitrophenyl)-, 1-(3-methylphenyl)-, 1-(3-ethylphenyl)-, (1-(3-trifluoromethylphenyl)-, 1-(4-methylphenyl)-, 1-(4-ethylphenyl)-, 1-(4-nitrophenyl)-, 1-(2-carbomethoxy-ethyl)-, 1-(2-carbethoxy-ethyl)-, 1-(2-carbo-n-propoxy-ethyl)-, 1-(2-carb-iso-propoxy-ethyl)-, 1-carbomethoxymethyl-, 1-carbethoxymethyl-, 1-carbo-n-propoxymethyl-, 1-carb-iso-propoxymethyl-, 1-(3-carbomethoxypropyl)-, 1-(3-carbethoxy-propyl)-, 1-methylcarbonylmethyl-, 1-ethylcarbonylmethyl-, 1-n-propylcarbonylmethyl-, 1-(2-methylcarbonylethyl)-, 1-(2-ethylcarbonylethyl)- and 1-(2-n-propylcarbonylethyl)-1,6-dihydro-3-hydroxy-6-thioxo-pyridazine.

The (thiono)(thiol)pyridazinephosphoric(phosphonic) acid esters and ester-amides (IV) to be used as starting materials are known from the literature and can be prepared in accordance with generally customary processes (see, for example, U.S. Pat. No. 2,759,937 and Netherlands Published Patent Application No. 7,411,406).

The following may be mentioned as individual examples: O,O-dimethyl-, O,O-diethyl-, O,O-di-n-propyl-, O,O-di-iso-propyl-, O,O-di-n-butyl-, O,O-di-sec.-butyl-, O,O-di-iso-butyl-, O-methyl-O-ethyl-, O-ethyl-O-n-propyl-, O-ethyl-O-iso-propyl-, O-ethyl-O-n-butyl-, O-ethyl-O-tert.-butyl-, O-n-propyl-O-n-butyl-, O-n-propyl-O-tert.-butyl- and O-n-propyl-O-sec.-butyl-O-(1,6-dihydro-1-methyl-6-oxo-pyradizin(3)yl)-phosphoric acid ester and the corresponding thiono analogues; O-methyl-S-methyl-, O-methyl-S-ethyl-, O-methyl-S-n-propyl-, O-methyl-S-iso-propyl-, O-methyl-S-butyl-, O-ethyl-S-methyl-, O-ethyl-S-ethyl-, O-ethyl-S-n-propyl-, O-ethyl-S-iso-propyl-, O-ethyl-S-butyl-, O-n-propyl-S-methyl-, O-n-propyl-S-ethyl-, O-n-propyl-S-n-propyl-, O-n-propyl-S-iso-propyl-, O-n-propyl-S-butyl-, O-iso-propyl-S-methyl-, O-iso-propyl-S-ethyl-, O-iso-propyl-S-n-propyl-, O-iso-propyl-S-iso-propyl-, O-iso-propyl-S-butyl-, O-n-butyl-S-methyl-, O-n-butyl-S-ethyl-, O-n-butyl-S-n-propyl-, O-n-butyl-S-iso-propyl-, O-n-butyl-S-butyl-, O-sec.-butyl-S-methyl-, O-sec.-butyl-S-ethyl-, O-sec.-butyl-S-n-propyl-, O-sec.-butyl-S-iso-propyl-, O-sec.-butyl-S-butyl-, O-sec.-butyl-S-butyl-, O-iso-butyl-S-ethyl-, O-iso-butyl-S-n-propyl-, O-iso-butyl-S-iso-propyl-, O-tert.-butyl-S-ethyl- and O-tert.-butyl-S-n-propyl-O-(1,6-dihydro-1-methyl-6-oxo-pyridazin(3)yl)-thiolphosphoric acid ester and the corresponding thiono analogues; O-methyl-N-methyl-, O-methyl-N-ethyl-, O-methyl-N-n-propyl-, O-methyl-N-iso-propyl-, O-methyl-N-butyl-, O-ethyl-N-methyl-, O-ethyl-N-ethyl-, O-ethyl-N-n-propyl-, O-ethyl-N-iso-propyl-, O-ethyl-N-n-butyl-, O-ethyl-N-sec.-butyl-, O-ethyl-N-iso-butyl-, O-ethyl-N-tert.-butyl-, O-n-propyl-N-methyl-, O-n-propyl-N-ethyl-, O-n-propyl-N-n-propyl-, O-n-propyl-N-iso-propyl-, O-n-propyl-N-butyl-, O-iso-propyl-N-methyl-, O-iso-propyl-N-ethyl-, O-iso-propyl-N-n-propyl-, O-iso-propyl-N-iso-propyl-, O-iso-propyl-N-butyl-, O-n-butyl-N-methyl-, O-n-butyl-N-ethyl-, O-n-butyl-N-n-butyl-, O-n-butyl-N-iso-propyl-, O-n-butyl-N-butyl-, O-sec.-butyl-N-ethyl-, O-sec.-butyl-N-n-propyl-, O-sec.-butyl-N-iso-propyl-, O-iso-butyl-N-methyl-, O-iso-butyl-N-ethyl-, O-iso-butyl-N-n-propyl-, O-iso-butyl-N-iso-propyl-, O-tert.-butyl-N-methyl-, O-tert.-butyl-N-ethyl-, O-tert.-butyl-N-n-propyl-, O-tert.-butyl-N-iso-propyl-, O-tert.-butyl-N-butyl- and O-tert.-butyl-N-iso-butyl-O-(1,6-dihydro-1-methyl-6-oxo-pyridazin(-3)yl)-phosphoric acid ester-amide and the corresponding thiono analogues; and O-methyl-methane-, O-methyl-ethane-, O-methyl-n-propane-, O-methyl-iso-propane-, O-methyl-n-butane-, O-methyl-iso-butane-, O-methyl-sec.-butane-, O-methyl-tert.-butane-, O-ethyl-methane-, O-ethyl-ethane-, O-ethyl-n-propane-, O-ethyl-iso-propane-, O-ethyl-n-butane-, O-ethyl-sec.-butane-, O-ethyl-iso-butane-, O-ethyl-tert.-butane-, O-ethyl-benzene-, O-n-propyl-methane-, O-n-propyl-ethane-, O-n-propyl-n-propane-, O-n-propyl-iso-propane-, O-n-propyl-n-butane-, O-n-propyl-sec.-butane-, O-n-propyl-iso-butane-, O-n-propyl-tert.-butane-, O-n-propyl-benzene-, O-iso-propyl-methane-, O-iso-propyl-ethane-, O-iso-propyl-n-propane-, O-iso-propyl-iso-propane-, O-iso-propyl-n-butane-, O-iso-propyl-sec.-butane-, O-iso-propyl-iso-butane-, O-iso-propyl-tert.-butane-, O-iso-propyl-benzene-, O-n-butyl-methane-, O-n-butyl-ethane-, O-n-butyl-n-propane-, O-n-butyl-iso-propane-, O-n-butyl-n-butane-, O-n-butyl-iso-butane-, O-n-butyl-sec.-butane-, O-n-butyl-tert.-butane-, O-iso-butyl-methane-, O-iso-butyl-ethane-, O-iso-butyl-n-propane-, O-iso-butyl-iso-propane-, O-iso-butyl-n-butane-, O-iso-butyl-iso-butane-, O-iso-butyl-sec.-butane-, O-iso-butyl-tert.-butane-, O-iso-butyl-benzene-, O-sec.-butyl-methane-, O-sec.-butyl-ethane-, O-sec.-butyl-n-propane-, O-sec.-butyl-iso-propane-, O-sec.-butyl-n-butane-, O-sec.-butyl-sec.-butane-, O-sec.-butyl-iso-butane-, O-sec.-butyl-tert.-butane-, O-sec.-butyl-phenyl-, O-tert.-butyl-methane-, O-tert.-butyl-ethane-, O-tert.-butyl-n-propane-, O-tert.-butyl-iso-propane-, O-tert.-butyl-butane- and O-tert.-butyl-phenyl-O-(1,6-dihydro-1-methyl-6-oxo-pyridazin(3)yl)-phosphonic acid diester and the corresponding thiono analogues.

Additional examples are those derivatives which, instead of being substituted by methyl in the 1-position, are substituted by ethyl, n-propyl, iso-propyl, 2-cyanoethyl, 1-cyanoethyl-, cyanomethyl, phenyl, 3-chlorophenyl, 2-chlorophenyl, 4-chlorophenyl, 3-nitrophenyl, 3-methylphenyl, 3-ethylphenyl, 3-trifluoromethylphenyl, 4-methylphenyl, 4-ethylphenyl, 4-nitrophenyl, 2-carbomethoxy-ethyl, 2-carbethoxyethyl, 2carbo-n-propoxy-ethyl, 2-carb-iso-propoxy-ethyl, carbomethoxymethyl, carbethoxymethyl, carbo-n-propoxymethyl, 3-carbomethoxypropyl, 3-carbethoxy-propyl, methylcarbonylmethyl, ethylcarbonylmethyl, n-propylcarbonylmethyl, 2-methylcarbonylethyl, 2-ethylcarbonylethyl or 2-n-propylcarbonyl-ethyl in the 1-position.

The process for the preparation of the compounds according to the invention is preferably carried out in the presence of a suitable solvent or diluent. Practically all inert organic solvents can be used for this purpose, especially aliphatic and aromatic, optionally chlorinated, hydrocarbons such as benzene, toluene, xylene, benzine, methylene chloride, chloroform, carbon tetrachloride or chlorobenzene; ethers, for example diethyl ether, dibutyl ether and dioxane; ketones, for example acetone, methyl ethyl ketone, methyl isopropyl ketone, and methyl isobutyl ketone; and nitriles, such as acetonitrile and propionitrile.

Any customary acid-binding agent can be used as the acid acceptor, when such is appropriate in process variant (a). Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

Examples of weakly basic compounds which are employed in process variant (b) are carbonates, such as sodium carbonate or potassium carbonate, or oxides, such as magnesium oxide.

The reaction temperatures in either process variant can be varied within a fairly wide range. In general, the reaction is carried out at between 0° and 120° C., preferably at 40° to 80° C., and is allowed to take place under normal pressure.

In carrying out variant (a), the starting materials are in general employed in the equimolar ratio. An excess of one or other component produces no significant advantages. The starting materials are in most cases reacted in one of the stated solvents, at elevated temperatures, if appropriate in the presence of an acid acceptor. After completion of the reaction, the mixture is filtered if necessary, and is poured into an organic solvent, for example toluene, and the organic phase is worked up in the usual manner by washing, drying and distilling off the solvent.

In process variant (b), the preferred procedure is to add a mixture of phosphorus pentasulfide and magnesium oxide to the phosphorous compound (IV) in a solvent and stir the batch at an elevated temperature until the reaction has ended. After filtration, the mixture is washed with sodium hydroxide solution and water and the organic phase is worked up as previously described.

The present compounds are, for the most part, obtained in the form of oils, which in some cases cannot be distilled without decomposition but are freed from the last volatile constituents by so-called "slight distillation," that is to say by prolonged heating under reduced pressure to moderately elevated temperatures, and are purified in this way. They are characterized by the refractive index. Some of the compounds are obtained in a crystalline form and are characterized by a sharp melting point.

As already mentioned, the (thiono)(thiol)-pyridazinephosphoric(phosphonic) acid esters and ester-amides according to the invention are distinguished by an excellent insecticidal and acaricidal activity. They are active against plant pests, pests harmful to health and pests of stored products and, in the veterinary medicine field, against animal parasites (ectoparasites) and combine a low phytotoxicity with a good action against both sucking and biting insects and against mites.

For this reason the compounds according to the invention can be employed successfully as pesticides in plant protection and in the hygiene field, the field of protection of stored products and the veterinary field.

The active compounds are well tolerated by plants, have a favorable level of toxicity to warm-blooded animals, and can be used for combating arthropod pests, especially insects and arachnidae, which are encountered in agriculture, in forestry, in the protection of stored products and of materials, and in the hygiene field. They are active against normally sensitive and resistant species and against all or some stages of development. The above-mentioned pests include: from the class of the Isopoda, for example *Oniscus asellus, Armadillidium vulgare* and *Porcellio scaber*, from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp., and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Phanolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., *Sitophilus Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aëdes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleiovora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all the flies were killed; 0% meant that no flies were killed.

The active compounds, the concentrations of the active compounds, the evaluation times and the results can be seen from the following table:

Table 1

| Active compounds | (Drosophila test) Active compound concentration in % | Degree of destruction in % after 1 day |
|---|---|---|
| (A) O—P(=S)(OCH₃)₂ on pyridazinone-N-phenyl | 0.1 / 0.01 / 0.001 | 100 / 60 / 0 |
| (B) O—P(=S)(OC₂H₅)₂ on pyridazinone-N-phenyl | 0.1 / 0.01 / 0.001 | 100 / 100 / 0 |
| (9) P(=S)(OC₂H₅)₂ with N—CH₃, C=S | 0.1 / 0.01 / 0.001 | 100 / 100 / 99 |
| (8) P(=S)(OC₂H₅)₂ with N—CH₃, C=S | 0.1 / 0.01 / 0.001 | 100 / 100 / 80 |
| (13) P(=S)(OC₂H₅)(phenyl) with N—CH₃, C=S | 0.1 / 0.01 / 0.001 | 100 / 100 / 99 |
| (17) P(=S)(OC₃H₇-iso)(CH₃) with N—CH₃, C=S | 0.1 / 0.01 / 0.001 | 100 / 100 / 98 |
| (10) P(=S)(OC₂H₅)(C₂H₅) with N-phenyl-CF₃, C=S | 0.1 / 0.01 / 0.001 | 100 / 100 / 100 |

EXAMPLE 2

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dripping wet and were then infested with mustard beetle larvae (Phaedon cochleariae).

After the specified periods of time, the degree of destruction was determined in %: 100% meant that all the beetle larvae had been killed whereas 0% meant that none of the beetle larvae had been killed.

The active compounds, the concentrations of the active compounds, the evaluation times and the results can be seen from the following table:

Table 2

| Active compounds | (Phaedon larvae test) Active compound concentration in % | Degree of destruction in % after 3 days |
|---|---|---|
| (A) O—P(=S)(OCH₃)₂ on pyridazinone-N-phenyl | 0.1 / 0.01 / 0.001 | 100 / 90 / 0 |
| (21) P(=S)(OC₄H₉-iso)(C₂H₅) with N—CH₃, C=S | 0.1 / 0.01 / 0.001 | 100 / 100 / 100 |

Table 2-continued (*Phaedon* larvae test)

| Active compounds | Active compound concentration in % | Degree of destruction in % after 3 days |
| --- | --- | --- |
| (15) | 0.1<br>0.01<br>0.001 | 100<br>100<br>100 |
| (5) | 0.1<br>0.01<br>0.001 | 100<br>100<br>100 |
| (12) | 0.1<br>0.01<br>0.001 | 100<br>100<br>100 |
| (11) | 0.1<br>0.01<br>0.001 | 100<br>100<br>100 |

EXAMPLE 3

Laphygma test
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% meant that all the caterpillars had been killed, whereas 0% indicated that no caterpillars had been killed.

The active compounds, the concentrations of the active compound, the evaluation times and the results can be seen from the following table:

Table 3

(*Laphygma* test)

| Active compound | Active compound concentration in % | Degree of destruction in % after 3 days |
| --- | --- | --- |
| (A) | 0.1<br>0.01<br>0.001 | 100<br>50<br>0 |
| (9) | 0.1<br>0.01<br>0.001 | 100<br>100<br>60 |
| (10) | 0.1<br>0.01<br>0.001 | 100<br>100<br>60 |
| (24) | 0.1<br>0.01<br>0.001 | 100<br>100<br>30 |
| (25) | 0.1<br>0.01<br>0.001 | 100<br>100<br>90 |

Table 3-continued
(*Laphygma* test)

| Active compound | Active compound concentration in % | Degree of destruction in % after 3 days |
|---|---|---|
| (5) [structure: O=P(S)(OC₃H₇-n)(C₂H₅) linked to pyridazine-thione with N-phenyl] | 0.1<br>0.01<br>0.001 | 100<br>100<br>60 |

EXAMPLE 4

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed, whereas 0% meant that none of the aphids were killed.

The active compounds, the concentrations of the active compounds, the evaluation times and the results can be seen from the following table:

Table 4
(*Myzus* test)

| Active compound | Active compound concentration in % | Degree of destruction in % after 1 day |
|---|---|---|
| (A) [structure: O=P(S)(OCH₃)₂ linked to pyridazinone with N-phenyl] | 0.1<br>0.01<br>0.001 | 99<br>30<br>0 |
| (C) [structure: O=P(O)(OC₂H₅)₂ linked to pyridazinone with N-phenyl] | 0.1<br>0.01<br>0.001 | 100<br>75<br>0 |

Table 4-continued
(*Myzus* test)

| Active compound | Active compound concentration in % | Degree of destruction in % after 1 day |
|---|---|---|
| (9) [structure: S=P(OC₂H₅)₂ linked to pyridazine-thione with N-CH₃] | 0.1<br>0.01<br>0.001 | 100<br>100<br>85 |
| (8) [structure: S=P(OC₂H₅)(C₂H₅) linked to pyridazine-thione with N-CH₃] | 0.1<br>0.01<br>0.001 | 100<br>100<br>80 |
| (17) [structure: S=P(OC₃H₇-iso)(CH₃) linked to pyridazine-thione with N-CH₃] | 0.1<br>0.01<br>0.001 | 100<br>100<br>80 |
| (21) [structure: S=P(OC₄H₉-iso)(C₂H₅) linked to pyridazine-thione with N-CH₃] | 0.1<br>0.01<br>0.001 | 100<br>98<br>98 |
| (16) [structure: S=P(OC₂H₅)(SC₃H₇-n) linked to pyridazine-thione with N-CH₃] | 0.1<br>0.01<br>0.001 | 100<br>100<br>60 |
| (15) [structure: S=P(OC₂H₅)(OC₃H₇-n) linked to pyridazine-thione with N-CH₃] | 0.1<br>0.01<br>0.001 | 100<br>100<br>98 |

Table 4-continued
(Myzus test)
| Active compound | Active compound concentration in % | Degree of destruction in % after 1 day |
|---|---|---|
| 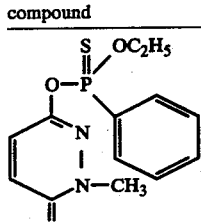 (13) | 0.1 / 0.01 / 0.001 | 100 / 100 / 99 |
| 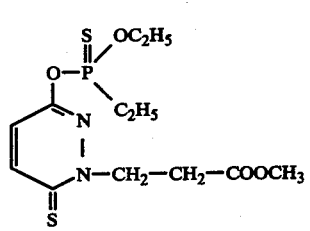 (20) | 0.1 / 0.01 / 0.001 | 100 / 98 / 90 |
|  (2) | 0.1 / 0.01 / 0.001 | 100 / 98 / 75 |
| 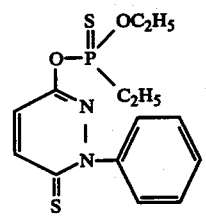 (4) | 0.1 / 0.01 / 0.001 | 100 / 99 / 99 |
| 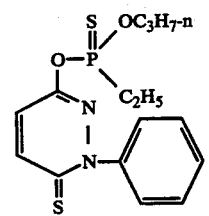 (5) | 0.1 / 0.01 / 0.001 | 100 / 99 / 98 |
| 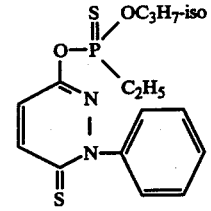 (7) | 0.1 / 0.01 / 0.001 | 100 / 100 / 75 |
| 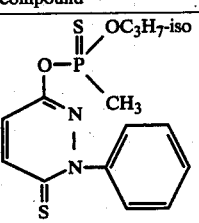 (6) | 0.1 / 0.01 / 0.001 | 100 / 100 / 70 |
| 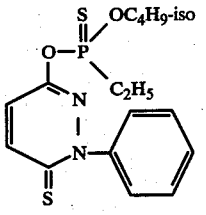 (23) | 0.1 / 0.01 / 0.001 | 100 / 100 / 95 |
| 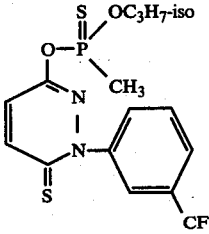 (12) | 0.1 / 0.01 / 0.001 | 100 / 100 / 80 |
| 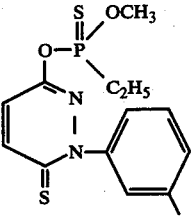 (11) | 0.1 / 0.01 / 0.001 | 100 / 100 / 99 |
| 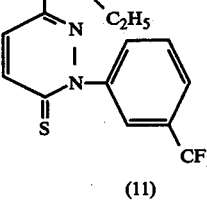 (30) | 0.1 / 0.01 / 0.001 | 100 / 100 / 70 |
| 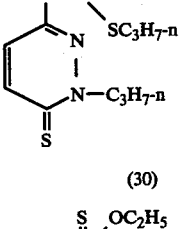 (31) | 0.1 / 0.01 / 0.001 | 100 / 100 / 95 |

EXAMPLE 5

Doralis test (systemic action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were watered with the preparation of the active compound so that this preparation penetrated into the soil without wetting the leaves of the bean plants. The active compound was taken up from the soil by the bean plants and thus passed to the infested leaves.

After the specified periods of time, the degree of destruction was determined as a percentage. 100% meant that all the aphids were killed; 0% meant that none of the aphids were killed.

The active compounds, the concentrations of the active compounds, the evaluation times and the results can be seen from the following table:

Table 5

(*Doralis* test / systemic action)

| Active compound | Active compound concentration in % | Degree of destruction in % after 4 days |
|---|---|---|
| 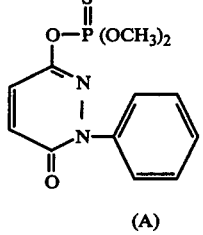 (A) | 0.1 | 0 |
| 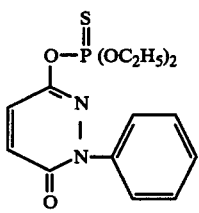 (B) | 0.1 | 0 |
| 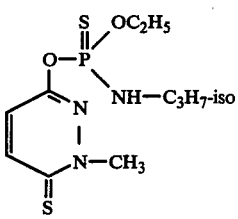 (14) | 0.1 | 100 |

Table 5-continued (*Doralis* test / systemic action)

| Active compound | Active compound concentration in % | Degree of destruction in % after 4 days |
|---|---|---|
| (18) | 0.1 | 100 |
| (29) | 0.1 | 100 |
| (9) | 0.1 | 100 |

EXAMPLE 6

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed, whereas 0% meant that none of the spider mites were killed.

The active compounds, the concentrations of the active compounds, the evaluation times and the results can be seen from the following table:

Table 6

(Tetranychus test)

| Active compound | Active compound concentration in % | Degree of destruction in % after 2 days |
|---|---|---|
| (C) diethyl phosphate structure | 0.1 | 20 |
| (9) | 0.1 / 0.01 | 98 / 50 |
| (8) | 0.1 / 0.01 | 98 / 70 |
| (17) | 0.1 / 0.01 | 100 / 100 |
| (21) | 0.1 / 0.01 | 99 / 40 |
| (4) | 0.1 / 0.01 | 100 / 95 |
| (6) | 0.1 / 0.01 | 100 / 99 |
| (23) | 0.1 / 0.01 | 98 / 20 |
| (24) | 0.1 / 0.01 | 90 / 50 |
| (10) | 0.1 / 0.01 | 100 / 20 |
| (12) | 0.1 / 0.01 | 100 / 100 |
| (11) | 0.1 / 0.01 | 100 / 100 |

Table 6-continued

(*Tetranychus* test)

| Active compound | Active compound concentration in % | Degree of destruction in % after 2 days |
|---|---|---|
| [structure (29): O-P(=S)(OC3H7-n)(C2H5) on pyridazine with 3-NO2-phenyl] | 0.1 | 98 |
|  | 0.01 | 90 |

EXAMPLE 7

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 7

(*Phorbia antiqua* grubs in the soil)

| Active compound | Degree of destruction in % at an active compound concentration of 10 ppm |
|---|---|
| (C) [O-P(=O)(OC2H5)2 on pyridazinone with phenyl] | 0 |
| (A) [O-P(=S)(OCH3)2 on pyridazinone with phenyl] | 0 |
| (5) [O-P(=S)(OC3H7-n)(C2H5) on pyridazinethione with phenyl] | 100 |
| (6) [O-P(=S)(OC3H7-iso)(CH3) on pyridazinethione with phenyl] | 100 |
| (7) [O-P(=S)(OC3H7-iso)(C2H5) on pyridazinethione with phenyl] | 100 |
| (8) [O-P(=S)(OC2H5)(C2H5) on pyridazinethione with N—CH3] | 100 |
| (9) [O-P(=S)(OC2H5)(OC2H5) on pyridazinethione with N—CH3] | 100 |

Table 7-continued
(Phorbia antiqua grubs in the soil)

| Active compound | Degree of destruction in % at an active compound concentration of 10 ppm |
|---|---|
| (10) | 100 |
| (11) | 100 |
| (13) | 100 |
| (14) | 100 |
| (15) | 100 |
| (17) | 100 |
| (21) | 100 |
| (23) | 100 |
| (24) | 100 |
| (25) | 100 |
| (26) | 100 |
| (27) | 100 |

EXAMPLE 8

Test insect: *Phaedon cochleariae*
Solvent: 3 parts by weight of actone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (= mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all the test insects had been killed and 0% when just as many test insects were still alive as in the case of the untreated control.

The active compounds, the amounts used and the results can be seen from the following table:

Table 8

| Active compound | (*Phaedon cochleariae* larvae) Degree of destruction in % at an active compound concentration of 10 ppm |
|---|---|
| 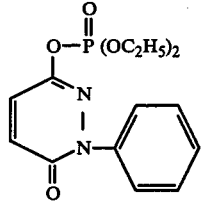 | 0 |
| 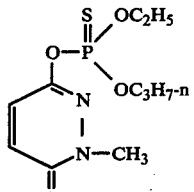 (15) | 100 |

EXAMPLE 9

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (= mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all the test insects had been killed and 0% when just as many test insects were still alive as in the case of the untreated control.

The active compounds, the amounts used and the results can be seen from the following table:

Table 9

| Active compound | (*Myzus persicae*) Degree of destruction in % at an active compound concentration of 10 ppm |
|---|---|
| 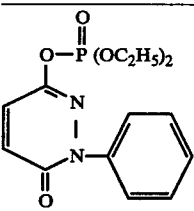 | 0 |
| 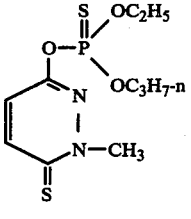 (15) | 100 |

EXAMPLE 10

LT$_{100}$ test for Diptera
Test insects: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 10

(LT$_{100}$ test for *Diptera/Musca domestica*)

| Active compound | Active compound concentration of the solution in % | LT$_{100}$ in minutes (') or hours (hrs) |
|---|---|---|
| (A) | 0.2 | 6 hrs = 0% |
| (C) | 0.02 | 6 hrs = 0% |
| (9) | 0.02 | 205' |
| (8) | 0.02 | 240' |
| (17) | 0.02 | 130' |

Table 10-continued (LT$_{100}$ test for *Diptera/Musca domestica*)

| Active compound | Active compound concentration of the solution in % | LT$_{100}$ in minutes (') or hours (hrs) |
|---|---|---|
| (21) | 0.02 | 6 hrs 80% |
| (24) | 0.02 | 6 hrs |
| (25) | 0.02 | 6 hrs = 80% |
| (10) | 0.02 | 6 hrs |

EXAMPLE 11

Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denoted that all the test insects had been killed; 0% denoted that no test insects had been killed.

The active compounds, the concentrations of the active compounds, the test insects and the results can be seen from the following table:

Table 11

(LT₁₀₀ test /*Sitophilus granarius*)

| Active compound | Active compound concentration of the solution in % | Degree of destruction in % |
|---|---|---|
| 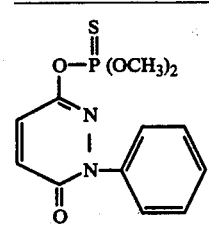 (A) | 0.2 | 0 |
| 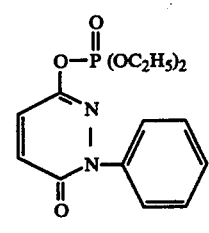 (C) | 0.02 | 0 |
| 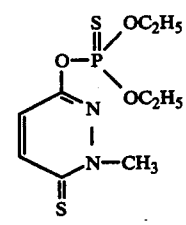 (9) | 0.02 | 100 |
| 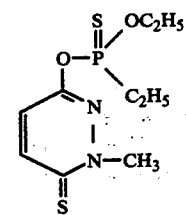 (8) | 0.02 | 100 |
| 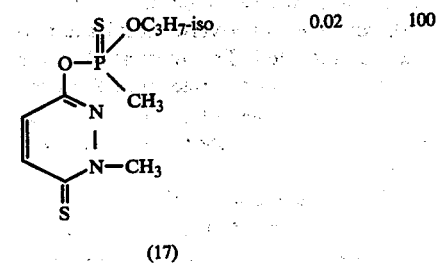 (17) | 0.02 | 100 |

Table 11-continued (LT₁₀₀ test /*Sitophilus granarius*)

| Active compound | Active compound concentration of the solution in % | Degree of destruction in % |
|---|---|---|
| (21) | 0.02 | 100 |
| (20) | 0.02 | 100 |
| (24) | 0.02 | 100 |
| (25) | 0.02 | 100 |
| (10) | 0.02 | 100 |
| (11) | 0.02 | 100 |

Table 11-continued
(LT$_{100}$ test /*Sitophilus granarius*)

| Active compound | Active compound concentration of the solution in % | Degree of destruction in % |
|---|---|---|
| (29) 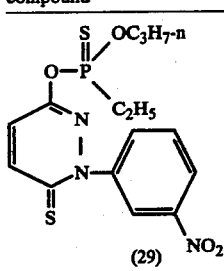 | 0.02 | 100 |
| (27) 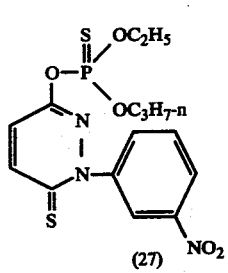 | 0.02 | 100 |

The process of the present invention is illustrated by the following preparative examples.

EXAMPLE 12

(a) The starting compounds (III) could be prepared, for example, in the following manner:

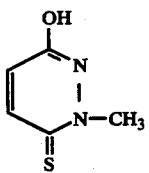

A mixture of 14.5 g (0.1 mole) of 1-methyl-3-chloro-1,6-dihydro-pyridazinone-(6) [for its preparation, see K. Eichenberger, A. Staehelin and J. Druey, Helv. Chim. Acta 37, 837 (1954)], 250 ml of toluene and 16.6 g (0.075 mole) of phosphorus pentasulfide was stirred for 4 hours at 70° C. The reaction mixture was then filtered, 10 g of silica gel were added to the filtrate, the mixture was again filtered and the filtrate evaporated under reduced pressure. The residue was boiled for 1 hour with a solution of 10 g of sodium hydroxide in 100 ml of water and the batch was then cooled and filtered. The filtrate was then brought to a pH value of about 3 with concentrated hydrochloric acid and the product which had precipitated was filtered off. 7.4 g (52% of theory) of 1-methyl-1,6-dihydro-3-hydroxy-6-thioxo-pyridazine were thus obtained in the form of yellow crystals of melting point 203° C.

(b)

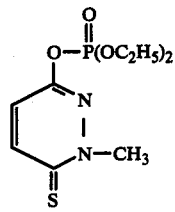

A mixture of 13.5 g (0.095 mole) of 1-methyl-1,6-dihydro-3-hydroxy-6-thioxo-pyridazine, 19.7 g (0.14 mole) of potassium carbonate, 16.4 g (0.095 mole) of O,O-diethylphosphoric acid diester chloride and 200 ml of acetonitrile was stirred for 4 hours at 45°–50° C. 300 ml of toluene were then poured into the reaction mixture, and the latter was shaken twice with 300 ml of water at a time. The organic phase was dried over sodium sulfate and was filtered off after adding 30 g of silica gel. The solvent was then stripped off under reduced pressure and the residue was subjected to slight distillation in a high vacuum at 80° C. 19 g (72% of theory) of O,O-diethyl-O-[1,6-dihydro-1-methyl-6-thioxopyridazin(3)yl]-phosphoric acid ester remain in the form of a brown oil having a refractive index $n_D^{26}$ of 1.5478.

EXAMPLE 13

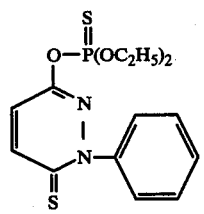

A mixture of 11 g (0.05 mole) of phosphorus pentasulfide and 11 g of magnesium oxide was added in portions to a solution of 34 g (0.1 mole) of O,O-diethyl-O-[1,6-dihydro-6-oxo-1-phenyl-pyridazin(3)yl]-thionophosphoric acid ester in 200 ml of toluene at 70° C. The batch was then stirred for a further 3 hours at 70° C., after which it was filtered. The filtrate was washed with 200 ml of 10% strength sodium hydroxide solution and then twice with 200 ml of water at a time.

The organic phase was dried over sodium sulfate and filtered after adding 30 g of silica gel. The solvent was then distilled off under reduced pressure and the residue was subjected to slight distillation in a high vacuum at 80° C. 14.9 g (42% of theory) of O,O-diethyl-O-[1,6-dihydro-1-phenyl-6-thioxo-pyridazin(3)yl]-thionophosphoric acid ester were thus obtained in the form of orange crystals of melting point 29°–30° C.

The following compounds of the formula

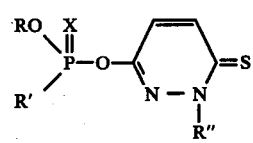

could be prepared analogously to Examples 12 and 13:

Table 12

| Compound No. | R | R' | R'' | X | Yield (% of theory) | Refractive index or M.p. [° C] |
|---|---|---|---|---|---|---|
| 3 | $C_2H_5$ | –Ph | –Ph | S | 50 | 77 |
| 4 | $C_2H_5$ | $C_2H_5$ | –Ph | S | 98 | $n_D^{20}$:1.6305 |
| 5 | $C_3H_7$-n | $C_2H_5$ | –Ph | S | 69 | $n_D^{20}$:1.6291 |
| 6 | $C_3H_7$-iso | $CH_3$ | –Ph | S | 60 | 55 |
| 7 | $C_3H_7$-iso | $C_2H_5$ | –Ph | S | 64 | $n_D^{21}$:1.6227 |
| 8 | $C_2H_5$ | $C_2H_5$ | $CH_3$ | S | 43 | $n_D^{21}$:1.5990 |
| 9 | $C_2H_5$ | $OC_2H_5$ | $CH_3$ | S | 55 | $n_D^{21}$:1.5718 |
| 10 | $C_2H_5$ | $OC_2H_5$ | –Ph-$CF_3$ | S | 64 | $n_D^{24}$:1.5695 |
| 11 | $CH_3$ | $C_2H_5$ | –Ph-$CF_3$ | S | 61 | $n_D^{24}$:1.5945 |
| 12 | $C_3H_7$-iso | $CH_3$ | –Ph-$CF_3$ | S | 51 | 75 |
| 13 | $C_2H_5$ | –Ph | $CH_3$ | S | 77 | 62 |
| 14 | $C_2H_5$ | $NH-C_3H_7$-iso | $CH_3$ | S | 79 | $n_D^{26}$:1.5897 |
| 15 | $C_2H_5$ | $OC_3H_7$-n | $CH_3$ | S | 75 | $n_D^{26}$:1.5791 |
| 16 | $C_2H_5$ | $SC_3H_7$-n | $CH_3$ | S | 81 | $n_D^{26}$:1.6094 |
| 17 | $C_3H_7$-iso | $CH_3$ | $CH_3$ | S | 53 | 93 |
| 18 | $CH_3$ | $OCH_3$ | $-CH_2-CH_2-CO-CH_3$ | S | 16 | $n_D^{28}$:1.5442 |
| 19 | $C_2H_5$ | $SC_3H_7$-n | $CH_2-CH_2-CN$ | S | 36 | $n_D^{24}$:1.6104 |
| 20 | $C_2H_5$ | $C_2H_5$ | $CH_2-CH_2-COOCH_3$ | S | 45 | $n_D^{26}$:1.5701 |
| 21 | $C_4H_9$-iso | $C_2H_5$ | $CH_3$ | S | 88 | $n_D^{24}$:1.5622 |
| 22 | $C_3H_7$-n | $C_3H_7$-iso | –Ph | S | 80 | $n_D^{24}$:1.5946 |
| 23 | $C_4H_9$-iso | $C_2H_5$ | –Ph | S | 78 | $n_D^{24}$:1.6081 |
| 24 | $C_2H_5$ | $OC_2H_5$ | –Ph-Cl | S | 59 | $n_D^{26}$:1.6128 |
| 25 | $C_2H_5$ | $OC_2H_5$ | –Ph-Cl | S | 72 | $n_D^{26}$:1.5989 |
| 26 | $C_2H_5$ | $OC_3H_7$-n | –Ph-$CH_3$ | S | 81 | $n_D^{26}$:1.6002 |
| 27 | $C_2H_5$ | $OC_3H_7$-n | –Ph-$NO_2$ | S | 62 | $n_D^{26}$:1.6103 |
| 28 | $C_2H_5$ | $SC_3H_7$-n | –Ph-$NO_2$ | S | 74 | $n_D^{26}$:1.6243 |
| 29 | $C_3H_7$-n | $C_2H_5$ | –Ph-$NO_2$ | S | 70 | $n_D^{26}$:1.6170 |
| 30 | $C_2H_5$ | $SC_3H_7$-n | $C_3H_7$-n | S | 62 | $n_D^{21}$:1.5965 |
| 31 | $C_2H_5$ | $SC_3H_7$-n | $C_3H_7$-iso | S | 33 | $n_D^{21}$:1.6014 |
| 32 | $C_2H_5$ | $SC_3H_7$-n | $C_2H_5$ | S | 49 | $n_D^{21}$:1.6002 |

Other compounds of formula I which can be similarly prepared include:

Table 13

| Compound No. | R | R' | R'' | X |
|---|---|---|---|---|
| 33 | C₂H₅ | SCH₃ | C₃H₇-i | O |
| 34 | C₂H₅ | NHCH₃ | 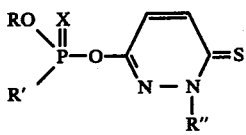 | O |
| 35 | C₂H₅ | OC₂H₅ | 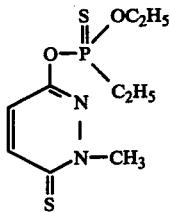 | O | and the like.

It will be appreciated that the instant specification and examples are set forth by way of illustration and not limitation, and that various modifications and changes may be made without departing from the spirit and scope of the present invention.

What is claimed is:

1. An O-alkyl-O-[1,6-dihydro-1-substituted-6-thioxopyridazin(3)yl]-(thiono)(thiol) phosphoric (phosphonic) acid ester or ester-amide of the formula

in which
R is alkyl with 1 to 6 carbon atoms,
R' is alkyl, alkoxy, alkylmercapto or alkylamino with 1 to 6 carbon atoms per alkyl chain, or phenyl,
R'' is alkyl, cyanoalkyl, carbalkoxyalkyl or alkylcarbonylalkyl with 1 to 4 carbon atoms per alkyl chain, phenyl or phenyl carrying at least one substituent selected from the group consisting of halogen, nitro, alkyl with 1 to 4 carbon atoms and halogenoalkyl with 1 to 4 carbon atoms, and
X is oxygen or sulfur.

2. A compound according to claim 1, in which
R is alkyl with 1 to 4 carbon atoms,
R' is straight-chain or branched chain alkyl, alkoxy, alkyl-mercapto or monoalkylamino each with 1 to 4 carbon atoms per alkyl chain, or phenyl,
R'' is methyl, ethyl, n-propyl, isopropyl, 2-cyanoethyl, 2-cyano-1-methyl-ethyl, cyanomethyl, or carbalkoxyalkyl or alkylcarbonylalkyl each with 1 to 3 carbon atoms per alkyl chain, or phenyl, or phenyl carrying at least one chlorine, nitro, methyl, ethyl or trifluoromethyl substituent, and
X is sulfur.

3. The compound according to claim 1 wherein such compound is O-ethyl-O-[1,6-dihydro-1-methyl-6-thioxopyridazin(3)yl]-ethanethionophosphoric acid ester of the formula

4. The compound according to claim 1 wherein such compound is O,O-diethyl-O-[1,6-dihydro-1-methyl-6-thioxopyridazin(3)yl]-thionophosphoric acid ester of the formula

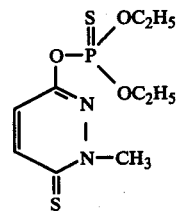

5. The compound according to claim 1 wherein such compound is O-ethyl-O-n-propyl-O-[1,6-dihydro-1-methyl-6-thioxopyridazin(3)yl]-thionophosphoric acid ester of the formula

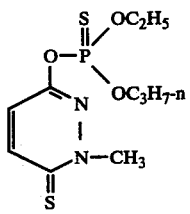

6. The compound according to claim 1 wherein such compound is O-isopropyl-O-[1,6-dihydro-1-methyl-6-thioxopyridazin(3)yl]-methanethionophosphonic acid ester of the formula

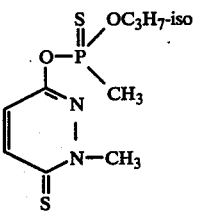

7. The compound according to claim 1 wherein such compound is O-isobutyl-O-[1,6-dihydro-1-methyl-6-thioxopyridazin(3)yl]-ethanethionophosphonic acid ester of the formula

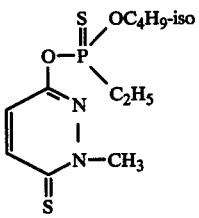

8. An arthropodicidal composition containing as active ingredient an arthropodicidally effective amount of a compound according to claim 1 in admixture with a diluent.

9. A method of combating insects and acarids which comprises applying to the insects, acarids, or to a habitat thereof, an insecticidally or acaracidally effective amount of a compound according to claim 1.

10. The method according to claim 9 in which said compound is

O-ethyl-O-[1,6-dihydro-1-methyl-6-thioxopyridazin(3)yl]-ethanethionophosphonic acid ester, O,O-diethyl-O-[1,6-dihydro-1-methyl-6-thioxopyridazin(3)yl]-thionophosphoric acid ester, O-ethyl-O-n-propyl-O-[1,6-dihydro-1-methyl-6-thioxopyridazin(3)yl]-thionophosphoric acid ester, O-isopropyl-O-[1,6-dihydro-1-methyl-6-thioxopyridazin(3)yl]-methanethionophosphonic acid ester, or O-isobutyl-O-[1,6-dihydro-1-methyl-6-thioxopyridazin(3)yl]-ethanethionophosphonic acid ester.

* * * * *